United States Patent [19]

Nogami et al.

[11] Patent Number: 4,822,168
[45] Date of Patent: Apr. 18, 1989

[54] SPECTROSCOPIC PHOTOMETER FOR FLOW THROUGH SAMPLE ABSORPTION

[75] Inventors: Taro Nogami; Tetsuyuki Miwa, both of Katsuta; Kenitiro Takahasi, Ibaraki, all of Japan

[73] Assignee: Hitachi, Ltd., Tokyo, Japan

[21] Appl. No.: 897,789

[22] Filed: Aug. 19, 1986

[30] Foreign Application Priority Data

Aug. 30, 1985 [JP] Japan .................................. 60-189621

[51] Int. Cl.⁴ .......................... G01J 3/42; G01J 3/427
[52] U.S. Cl. .................................... 356/319; 356/320; 356/411
[58] Field of Search ............... 356/411, 334, 319, 320, 356/307, 328

[56] References Cited

U.S. PATENT DOCUMENTS

| | | | |
|---|---|---|---|
| 2,734,418 | 2/1956 | Enns | 356/307 |
| 4,030,828 | 6/1977 | Sonobe et al. | 356/334 X |
| 4,279,511 | 7/1981 | Maute et al. | 356/334 X |
| 4,367,041 | 1/1983 | Webb, Jr. et al. | 356/411 X |
| 4,557,601 | 12/1985 | Kuroishi et al. | 356/320 |

FOREIGN PATENT DOCUMENTS 58-102114  6/1983  Japan .................................. 356/319

Primary Examiner—Vincent P. McGraw
Attorney, Agent, or Firm—Antonelli, Terry & Wands

[57] ABSTRACT

An analyzing apparatus provided with a spectroscopic photometer, in which light emitted by a deuterium lamp enters a flow cell; light transmitted by the flow cell is divided into two light beams by means of a beam splitter, one of which is received by a detecting element for sample measurement and the other of which is received by a detecting element for monitoring through a filter transmitting only light in a predetermined wavelength region, which is not essentially absorbed by the sample; and a signal processing device compares the output signal of the detecting element for sample measurement with that of the detecting element for monitoring and effects necessary operations.

14 Claims, 6 Drawing Sheets

F I G. 2
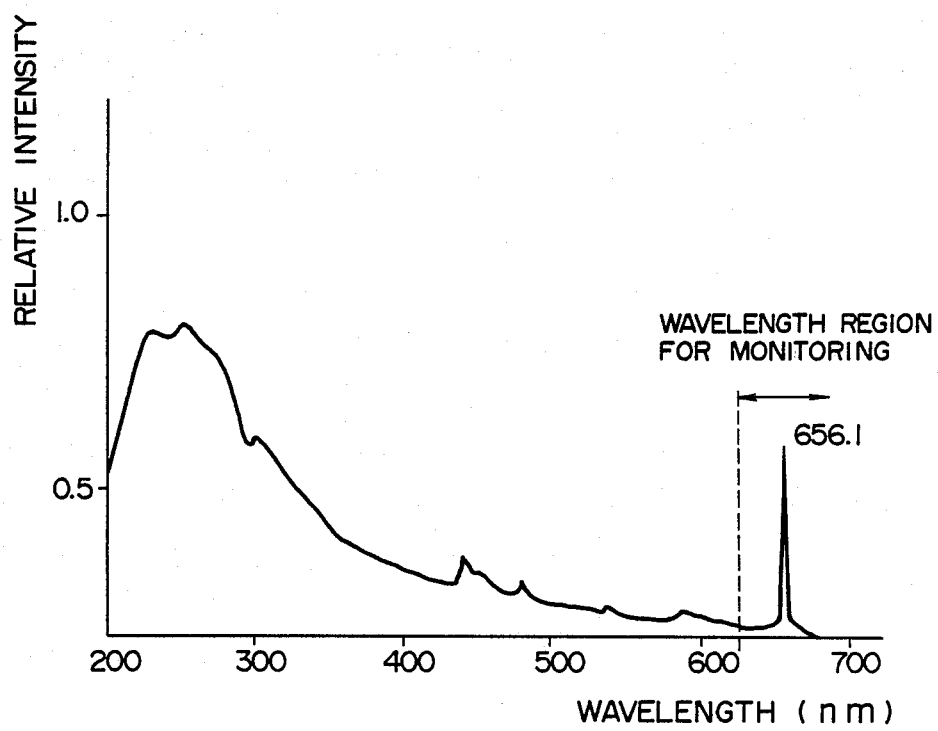

4,822,168

SPECTROSCOPIC PHOTOMETER FOR FLOW THROUGH SAMPLE ABSORPTION

BACKGROUND OF THE INVENTION

This invention relates to an analyzing apparatus provided with a spectroscopic photometer, and in particular to an analyzing apparatus for measuring transmission light passing through a flow cell, through which a sample to be studied flows, by means of a detecting element for monitoring and a detecting element for sample measurement.

There are known various sorts of analyzing apparatuses, which has a flow cell and in which a spectroscopic photometer is incorporated as a detector. A liquid chromatographic analyzing apparatus, a flowing injection analyzing apparatus and an automatic biochemical analyzing apparatus for clinical use may be enumerated as representatives of this sort of apparatuses.

In an analyzing apparatus having a flow cell a beam splitter is disposed generally between a light source and the flow cell, and influences of variations in the light source are corrected by monitoring reference light taken out therefrom. When such an analyzing apparatus is used e.g. in a liquid chromatograph, variations in base line cannot be eliminated satisfactorily and in particular measurement accuracy is bad in a region, where absorbance is low. It is thought that this may be attributed to the following two reasons.

The first of them concerns variations in the light source. One of the two light beams formed by dividing incident light by means of the beam splitter enters a sample cell and the other the detector on the monitor side. When the light emitting point of the light source fluctuates geometrically, influences of the fluctuations on these two light beams are not identical. Particularly, in the case where the sample cell is a flow cell having a small volume for liquid chromatograph, in general it gives rise to an unbalance that slight geometrical fluctuations in the light emitting point of the light source have large influences on the small volume flow cell side and little influences on the detector on the monitor side having a light receiving surface, which is considerably large with respect to that of the small volume flow cell. Further, if two exit slits of the spectroscopic analyzer are disposed separately for the monitor side and for the sample side or if gaps are disposed intentionally on both the light paths or on one of them, it is extremely difficult to harmonize relation between slight deviations of the optical axis due to the fluctuations in the light emitting point of the light source and the gaps for the two optical paths. Therefore, it is not possible for the prior art techniques to correct satisfactorily errors due to fluctuations in the light source.

The second reason concerns flow of the solution in the flow cell. For example, fluctuations in light transmitted by the flow cell due to variations in the reflective index of the solution flowing through the flow cell often give rise to problems in a photometer for liquid chromatograph. In such a photometer, where light for the monitor is split before the flow cell, it is not possible to eliminate such variations of the transmitted light due to the flow cell. U.S. Pat. No. 4,557,601 has disclosed an analyzing apparatus, in which the transmitted light is measured by means of a spectroscopic photometer after having made light emitted by a light source pass through the flow cell. According thereto, the absorbance is measured by comparing a photometrically measured value at a wavelength corresponding to a peak portion in the absorption spectrum with a photometrically measured value at a wavelength, where the absorbance is small.

The absorbance is represented by logarithm of the ratio S/R of the detected signal S obtained by the detecting element for sample measurement to the detected signal R obtained by the detecting element for monitoring. In this case, it is desirable to use for the signal detected for the monitoring light at a wavelength, where no absorption is produced by the sample flowing through the flow cell. Usually a deuterium lamp is used as the light source in an analyzing apparatus provided with a spectroscopic photometer. In the case where a deuterium lamp is used, the emitted light intensity in its emission spectrum decreases with increasing wavelength, as indicated in FIG. 2. Furthermore, almost all the absorption peaks of samples obtained from liquid chromatograph, etc. are in a wavelength region under 600 nm. Consequently it is desirable to use light having a wavelength longer than 600 nm for the monitor. However, since the detected signal at a certain wavelength is small in the long wavelength region, the value of the denominator is the ratio S/R used for the absorbance calculation, i.e. the detected signal for the monitor is extremely small. The result obtained by this ratio calculation is apt to be influenced by noise and the noise level of data is, therefore, very high.

SUMMARY OF THE INVENTION

The object of the invention is to provide an analyzing apparatus provided with a spectroscopic photometer permitting to correct optical variations due to flow of the sample flowing through the flow cell, at the same time to reduce influences of fluctuations in the light source and to effect absorbance measurements with a high S-N ratio.

According to this invention, the light transmitted by the flow cell is divided into light directed to the detecting element for sample measurement and that directed to the detecting element for monitoring total light energy in a certain wavelength region, where practically no light is absorbed by the sample, and the total light energy in this wavelength region is detected as a monitor signal. More in detail the analyzing apparatus according to this invention is so constructed that light having a large wavelength, which is practically not absorbed by the sample, is detected by the detecting element for the monitor.

BRIEF DESCRIPTION OF THE DRAWINGS

FIG. 2 is a diagram indicating detected light intensity vs. wavelength, in the case where light emitted by a deuterium lamp is received by a silicon photocell;

DESCRIPTION OF THE PREFERRED EMBODIMENTS

Figure 1:
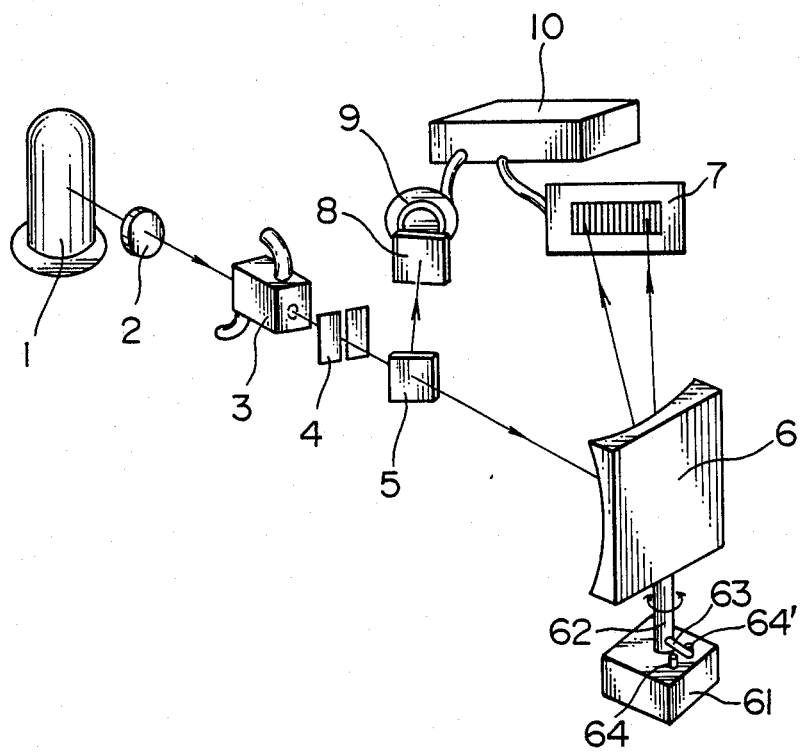
FIG. 1 is a scheme illustrating the construction of the photometer portion in an embodiment of this invention.

An embodiment of this invention will be explained, referring to FIG. 1.

Light emitted by a deuterium lamp 1 is focused by a lens 2, enters a flow cell 3 through an end surface of the cell and traverses a sample. Then, passing through an entrance slit 4, it enters a spectroscope, where a part of it is directed to the monitor side by a beam splitter 5. The light on the optical path of the monitor side passes through a short-cut filter 8 for cutting off more than a half of ultra-violet and visible light. The short-cut filter 8 is made of an optical material permitting principally only light over 630 nm to pass therethrough. Light transmitted by the beam spitter 5 enters a concave diffraction grating 6 and is dispersed. As the result, a slit image is formed on the light receiving surface of a photodiode array 7 disposed on the slit image surface for every wavelength. The photodiode array is of self scanning type and the output signal for every bit enters an electronic circuit system 10 in the form of a pulse train. On the other hand a short-cut filter 8 of 630 nm and a silicon photocell 9 are disposed on the monitor side and the output signal of the silicon photocell 9 enters the signal processor system 10, too. Inside of the signal processor system 10, a divisional operation dividing the output signal of each element of the photodiode array 7 by the output signal of the silicon photocell 9 is effected and then a logarithmic transformation is performed. The signal thus obtained representing the absorbance is A/D transformed and other necessary data processing is effected. In addition, the concave diffraction grating 6 is fixed to a rotating shaft 62, which can rotate in two directions. The rotation of the rotating shaft 6 may have a stopping pin 63, which is stopped by stoppers 64 and 64' at two predetermined positions. In this way, when the wavelength region of the light received by a photodiode array 7 cannot cover the whole wavelength region necessary for the measurement, the measurement range can be changed for two wavelength regions.

FIG. 2 is a diagram indicating detected light intensity vs. wavelength in the case where light emitted by a deuterium lamp is received by a silicon photocell. When light under 630 nm is cut off by the filter 8 disposed on the optical path of the monitor side, in practice, light including a line of 656.1 nm enters the silicon photocell 9 on the monitor side. However, in usual samples to be measured such as liquid chromatograph, etc. no strong absorption peaks exist in this wavelength range. That is, the greatest part of the energy transition in an object sample such as liquid chromatograph, etc. is excitation to an antibonding $\pi$ orbit, i.e. $\pi \rightarrow \pi^*$, $n \rightarrow \pi^*$, and almost all the absorption peaks exist under 600 nm. Consequently, although light transmitted by the sample is monitored, influences of the absorption by the sample on the monitor signal are negligible in almost all cases. Therefore, by using such a monitor signal, it is possible to effect a relative photometry without any difficulty.

By such a relative photometry, firstly, even in the case where the arc in the deuterium lamp fluctuates slightly in position, since the monitor portion is behind small gaps, such as the flow cell 3 and the slit 4, influences of fluctuations on the main optical path and on the monitor optical path appear approximately equally. As the result errors due to fluctuations in the light source are properly corrected and thus stable measurements are possible, even in the region, where absorbance is low. Secondly, since the monitor portion is behind the flow cell, it is possible to correct fluctuations due to non-uniformity of the refractive index in the liquid flowing in the flow cell. Thirdly, since the detecting element for the monitor detects light in a predetermined wavelength region, where no light is absorbed by the sample in the flow cell, in the form of a value obtained by integrating the total light energy over the whole monitoring wavelength region, it is possible to obtain enough monitor signal level including noise only slightly.

Figure 3:
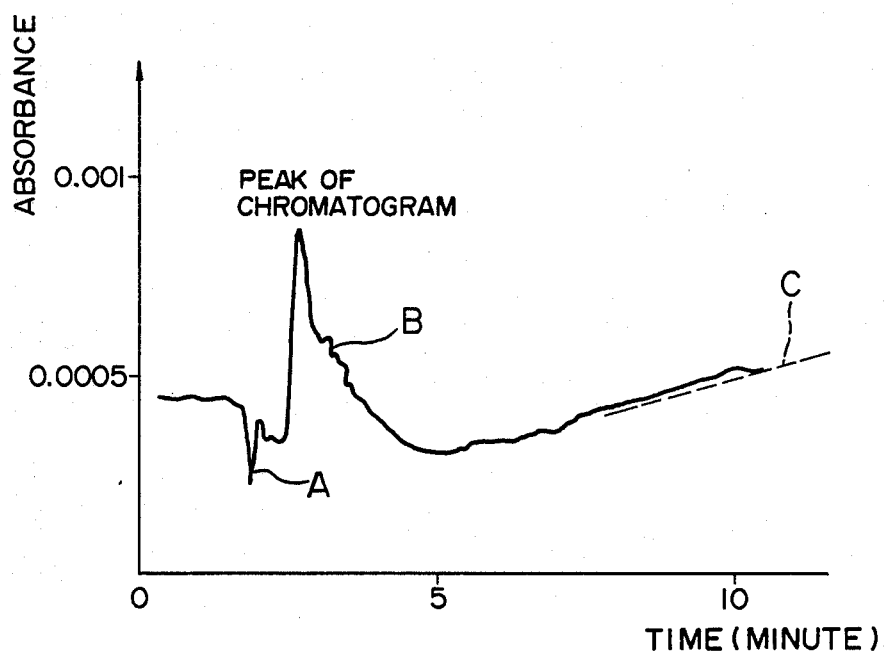
FIG. 3 is a diagram for explaining variations superposed on data.

FIG. 3 is a diagram for explaining various variations superposed on data in a chromatogram recording. In the figure, A indicates variations due to influences of fluctuations in the refractive index of the liquid, and B and C indicate variations due to fluctuations in the light source. All of these variations can be corrected by the method described in the above embodiment.

Figure 4:
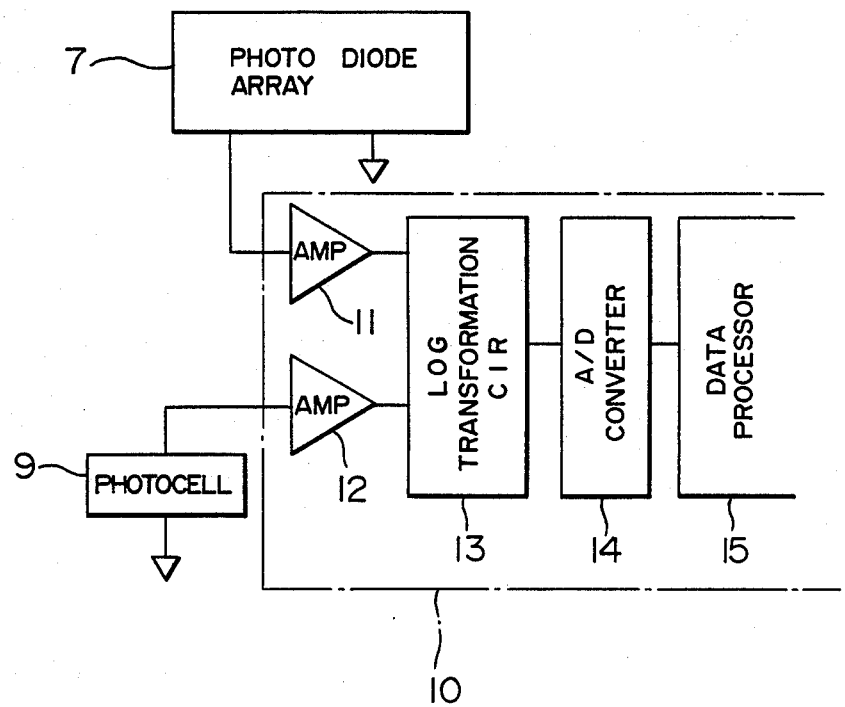
FIG. 4 is a block diagram for explaining the electronic circuit in the apparatus illustrated in FIG. 1.

FIG. 4 is a block diagram for explaining the function of the electronic circuit system 10. The pulse train, which is an output signal of the photodiode array 7, enters a video amplifier 11 constituted as a wide band amplifier. The signal enters LOG transformation circuit 13 through one of two input terminals after having being amplified in the video amplifier 11. On the other hand the output signal of the silicon photocell 9 is amplified by a preamplifier 12 and enters the LOG transformation circuit 13 through the other input terminal. The output signal of the LOG transformation circuit 13 is a signal representing the difference between the two values obtained by LOG transformation of the two input signals. That is, it represents a value obtained by LOG transformation of the ratio of the two input signals. This value is transformed into a digital signal by means of an A/D converter 14 and then enters a data processing portion 15. The data processing portion 15 enables chromatogram recording, chromatogram memory, spectrum memory, spectrum recording, operations between different spectrums, etc.

Figure 5:
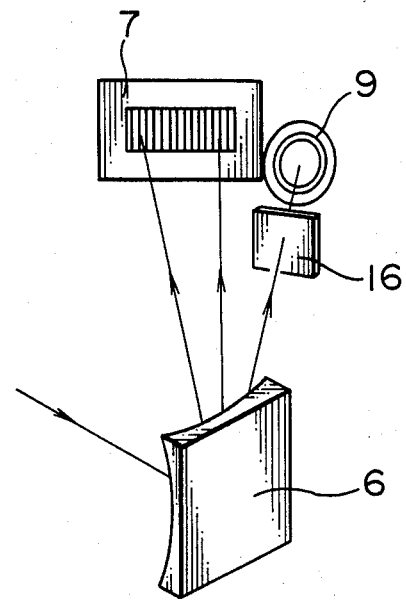
FIG. 5 is a scheme illustrating the construction of the principal part in another embodiment of this invention.
Figure 6:
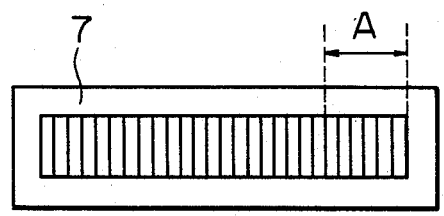
FIG. 6 is a scheme for explaining the principal part of a modified example of the embodiment of this invention indicated in FIG. 5.

FIG. 5 is a scheme illustrating the construction of the principal part in a second embodiment of this invention. In this embodiment no beam splitter is used and the silicon photocell 9 for monitoring is disposed on the long wavelength side of the slit image surface and has a light receiving portion, which is so large that long wavelength light transmitted by a cut-off filter 16 for cutting off secondary light is sufficiently received. Although a separate detector is used for the monitor in FIG. 5, it is also possible to increase the number of channels of the photodiode array 7, as indicated in FIG. 6, and to construct it so that long wavelength light for the monitor itself is received by channels in a part A of the photodiode array. In this case the signal for monitoring is obtained in the form of a integrated value by adding all the signals detected by the photodiodes in the part A.

Figure 7:
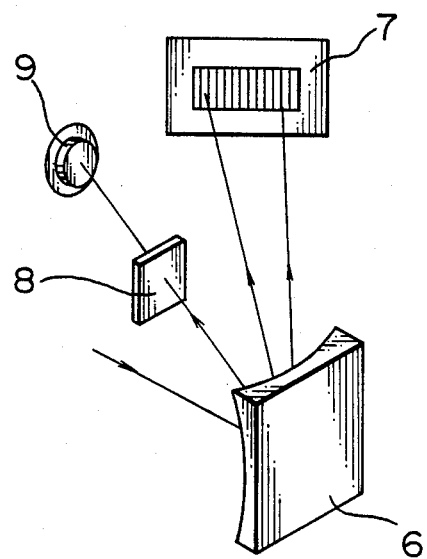
FIG. 7 is a scheme illustrating the construction of the principal part in still another embodiment of this invention.

FIG. 7 illustrate a third embodiment of this invention. The silicon photocell 9 is arranged at the position of the 0-th order light in the slit image surface. In this way, long wavelength light hardly absorbed by the sample in the 0-th order light passes through the short-cut filter 8 and enters the silicon photocell 9 for monitoring. Also in this case, as indicated in FIG. 6, no separate detector is used for the monitor and the photodiode array 7 can be constructed so as to receive the 0-th order light described above by itself.

Either of the embodiments indicated above in FIGS. 1, 5 and 7 can be incorporated in an analyzing apparatus as a liquid chromatograph detection portion. In this case liquid containing samples obtained by separating components from each other by means of a separation column is made to flow in the flow cell 3 and continuously therethrough.

In a prior art photodiode array for liquid chromatograph, when liquid flows through the phototcell, fluctuations of 0.001 Au (Absorbance unit)-0.01 Au, calculated in terms of the absorbance are produced. To the contrary, according to this invention, the fluctuations are reduced to 0.0002 Au-0.001 Au. By this fact restrictions on the methodology of the liquid chromatograph are reduced (it becomes necessary to restrict the nature of the solvent, the method how to set the gradient, the amount of the sample to be injected, etc.), and as the result good influences on the amelioration of the efficiency and the economic utility can be obtained.

According to this invention, since it is possible to influencies of fluctuations due to flow through the flow cell and those of fluctuations in the light source, measurements with a high precision are possible even in a region, where the absorbance is low.

We claim:

1. An analyzing apparatus provided with a spectroscope photometer comprising:
   a deuterium lamp for providing light;
   a flow cell, through which a sample flows and light from said deuterium lamp passes;
   means for spectroscopically dispersing light passing through said flow cell;
   detector means for sample measurement being disposed for receiving light dispersed by said dispersing means;
   detector means for monitoring being disposed for receiving light passed through said flow cell within a predetermined wavelength region of a plurality of wavelengths longer than a wavelength region essentially absorbed by said sample so as to obtain a total light energy sufficient to reduce effects of noise in a monitoring signal; and
   operation means comparing the output signal of said detector means for sample measurement with that of said detector for monitoring.

2. An analyzing apparatus provided with a spectroscopic photometer according to claim 1, in which said detector means for monitoring includes a filter, which is so formed that only light in the predetermined wavelength region passes through it, and a detecting element receiving light, which has passed through said filter.

3. An analyzing apparatus provided with a spectroscopic photometer according to claim 2, in which said filter includes means, which is so constructed that only light having a wavelength longer than that detected by said detector means for sample measurement can pass therethrough.

4. An analyzing apparatus provided with a spectroscopic photometer according to claim 1, wherein said dispersion means includes a light dispersing element, which disperses said light passed through said flow cell depending on the wavelength, and said detector means for sample measurement includes a detecting element for sample measurement, which receives only light in another predetermined wavelength region in the light dispersed by said light dispersing element.

5. An analyzing apparatus provided with a spectroscopic photometer according to claim 4, in which said detecting element for sample measurement is an array of light receiving elements.

6. An analyzing apparatus provided with a spectroscopic photometer according to claim 4, in which said detecting element for monitoring includes a detecting element for monitoring, which is so disposed that it receives only light in the predetermined wavelength region having the wavelength longer than that received by said detecting element for sample measurement in said light dispersed by said dispersing element.

7. An analyzing apparatus provided with a spectroscopic photometer according to claim 6, in which said detecting element for monitoring includes a light receiving surface having a light receiving area, sufficiently large to receive light in said predetermined wavelength region.

8. An analyzing apparatus provided with a spectroscopic photometer according to claim 6, in which said detecting element for monitoring and said detecting element for sample measurement are incorporated in one array of light receiving elements.

9. An analyzing apparatus provided with a spectroscopic photometer according to claim 6, in which said detecting means for monitoring includes a filter disposed before said detecting element for monitoring, said filter transmitting only light in said predetermined wavelength region and cutting off secondary light.

10. An analyzing apparatus provided with a spectroscopic photometer according to claim 4, in which said dispersing element is a diffraction grating and said detecting means for monitoring comprises a detecting element disposed at a position, which 0-th order light in the light dispersed by said light dispersing element passes through, and a filter transmitting only light in said predetermined wavelength region in said 0-th order light.

11. An analyzing apparatus provided with a spectroscopic photometer according to claim 4, in which said light dispersing element includes means, which selectively locates said light dispersing element at least at two predetermined rotational positions.

12. An analyzing apparatus provided with a spectroscopic photometer according to claim 1, in which said operation means includes a circuit, which transforms the output signal of said detector means for sample measurement and that of said detector means for monitoring into a logarithm and subtracts the second transformed signal thus obtained from the first.

13. An analyzing apparatus provided with a spectroscopic photometer comprising:
   a deuterium lamp for producing light;
   a flow cell, through which a sample flows and light from said deuterium light passes;
   means for spectroscopically dispersing light passing through said flow cell;
   detector means for sample measurement disposed for receiving light dispersed by said dispersing means;
   detector means for monitoring disposed for receiving light passed through said flow cell in a predetermined wavelength region longer than a wavelength region essentially absorbed by said sample;
   operation means comparing the output signal of said detector means for sample measurement with that of said detector means for monitoring; and
   a beam splitter dividing said light passed through said flow cell into light directed to said dispersing means and that directed to said detector means for monitoring.

14. An analyzing apparatus provided with a spectroscopic photometer comprising:
    a deuterium lamp for providing light;
    a flow cell, through which a sample flows and light from said deuterium lamp passes;
    means for spectroscopically dispersing light passing through said flow cell;
    detector means for sample measurement being disposed for receiving light dispersed by said dispersing means;
    detector means for monitoring being disposed for receiving light passed through said flow cell within a predetermined wavelength region of a plurality of wavelengths longer than a wavelength region essentially absorbed by said sample, said predetermined wavelength region longer than said wavelength region essentially absorbed by said sample being a wavelength region greater than 600 nm; and
    operation means comparing the output signal of said detector means for sample measurement with that of said detector for monitoring.

* * * * *